United States Patent
Ott et al.

(10) Patent No.: US 9,381,312 B1
(45) Date of Patent: Jul. 5, 2016

(54) INSUFFLATION APPARATUS

(76) Inventors: Douglas E. Ott, Macon, GA (US);
Nathan Tran, Apple Valley, MN (US)

( * ) Notice: Subject to any disclaimer, the term of this patent is extended or adjusted under 35 U.S.C. 154(b) by 577 days.

(21) Appl. No.: 13/065,438

(22) Filed: Mar. 22, 2011

Related U.S. Application Data

(63) Continuation-in-part of application No. 12/381,978, filed on Mar. 18, 2009.

(51) Int. Cl.
*A61M 13/00* (2006.01)

(52) U.S. Cl.
CPC .................................. *A61M 13/003* (2013.01)

(58) Field of Classification Search
CPC .......... A61M 16/16; A61M 2016/109; A61M 13/003; A61M 2202/02; A61M 3/003; A61M 2202/0007; A61M 16/109; A61M 2202/0225; A61M 2202/0208; A61M 13/00; A61M 16/105; A61M 16/1095; A61M 2205/75; A61M 16/0875; A61M 2005/006; A61M 5/165; A61M 11/02; A61M 16/0808; A61M 16/1045; A61M 2205/3372; A61M 16/142; A61M 16/108; A61M 16/1085; A61M 16/161; A61M 2205/3344; A61M 17/3474; A61M 2017/3437; B01D 19/0031
USPC ................. 604/23, 26, 164.01–167, 264, 158
See application file for complete search history.

(56) References Cited

U.S. PATENT DOCUMENTS

| 5,411,474 | A | * | 5/1995 | Ott et al. .......................... 604/26 |
| 5,746,720 | A | * | 5/1998 | Stouder, Jr. .................... 604/117 |
| 6,010,118 | A | | 1/2000 | Milewicz |
| 6,814,714 | B1 | | 11/2004 | Novak |
| 2004/0102731 | A1 | | 5/2004 | Blackhurst |
| 2004/0254524 | A1 | | 12/2004 | Spearman |
| 2005/0015043 | A1 | * | 1/2005 | Stubbs et al. ................... 604/26 |
| 2005/0113797 | A1 | | 5/2005 | Ott |
| 2006/0129098 | A1 | | 6/2006 | Hart |
| 2007/0088274 | A1 | | 4/2007 | Stubbs |
| 2007/0088275 | A1 | * | 4/2007 | Stearns et al. ........... 604/164.01 |
| 2010/0241061 | A1 | * | 9/2010 | Ott et al. .......................... 604/26 |

FOREIGN PATENT DOCUMENTS

WO  WO 2010-107464  9/2010

\* cited by examiner

*Primary Examiner* — Bhisma Mehta
*Assistant Examiner* — Brandy S Lee
(74) *Attorney, Agent, or Firm* — Jacobson and Johnson; Thomas N Phung

(57) ABSTRACT

An insufflation apparatus and/or insufflation kit for use during a medical procedure including a fluid stabilizer wherein the insufflation apparatus can be used in different modes with a mode change between needle insufflation or cannula insufflation accomplished without having to use a different fluid stabilizer or a different trocar wherein the trocar may be a gas conditioning trocar having a chamber for on-the-go heating and hydrating an unconditioned insufflation gas prior to injecting a conditioned insufflation gas into a body cavity.

5 Claims, 7 Drawing Sheets

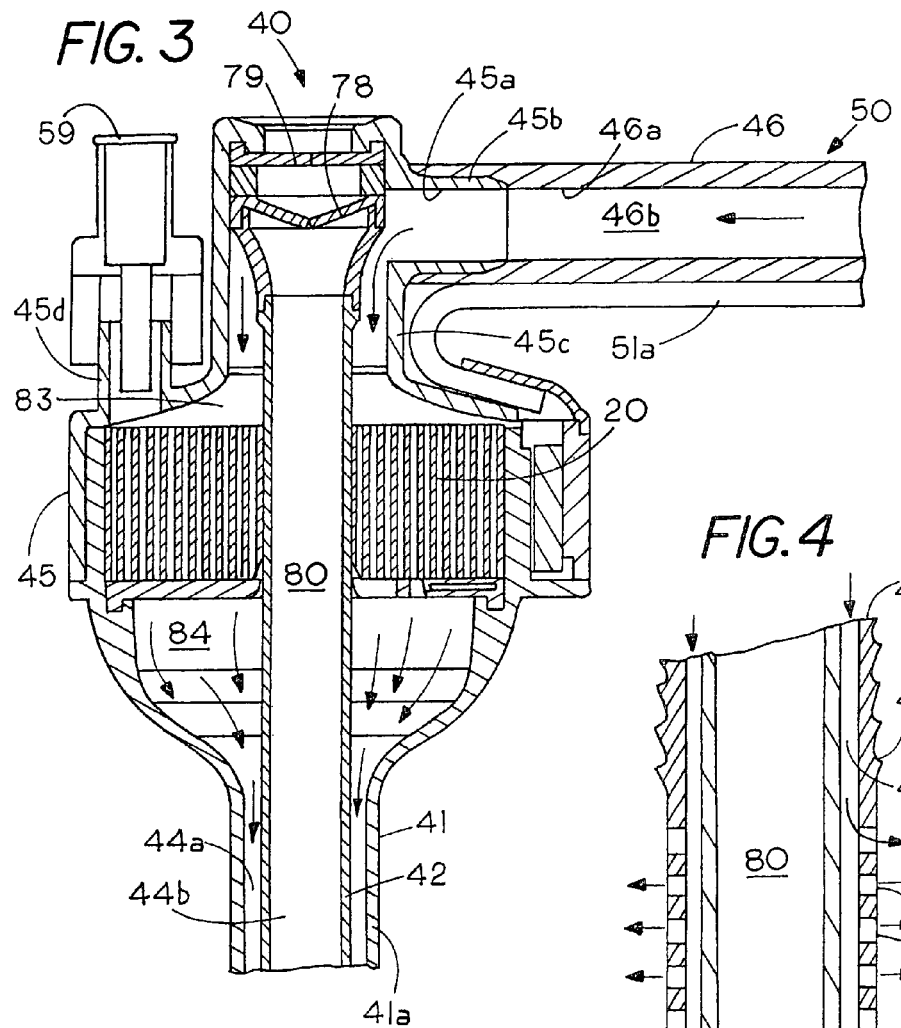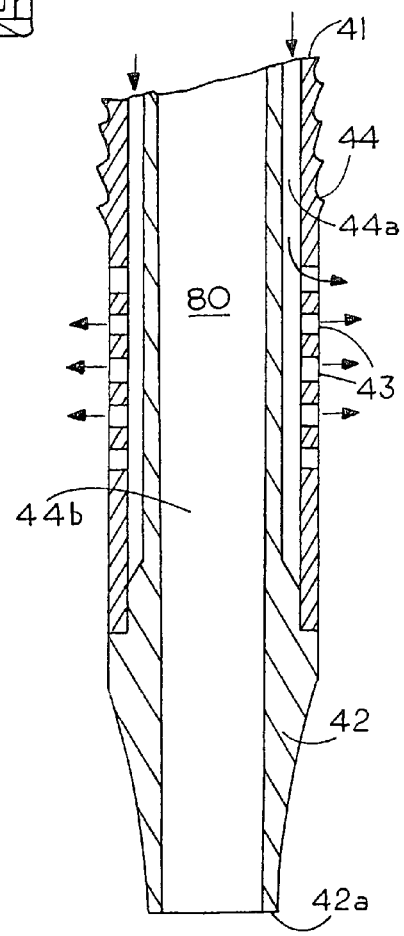

INSUFFLATION APPARATUS

CROSS REFERENCE TO RELATED APPLICATIONS

This application is a continuation in part of U.S. application Ser. No. 12/381,978 titled GAS CONDITIONING TROCARS filed Mar. 18, 2009.

STATEMENT REGARDING FEDERALLY SPONSORED RESEARCH OR DEVELOPMENT

None

REFERENCE TO A MICROFICHE APPENDIX

None

FIELD OF THE INVENTION

This invention relates to the field of medical devices and, more specifically, to a medical insufflation apparatus that includes a trocar and a fluid stabilizer for delivery of conditioned gas to a body cavity while minimizing or eliminating adverse flow conditions which may be induced by conventional medical insufflation apparatus.

BACKGROUND OF THE INVENTION

The concept of a medical apparatus for humidifying or otherwise treating a gas from an insufflator during surgery is described in Douglas Ott et al. U.S. Pat. Nos. 5,411,474; 6,068,609 and 7,066,902. Briefly, an insufflation gas is heated and hydrated i.e. conditioned, before the gas is directed into a body cavity through a device such as a trocar. In order to hydrate the insufflation gas a charge of hydration fluid is typically injected into a device where the hydration fluid can humidify the insufflation gas and a heater can bring the insufflation gas to a temperature near body temperature. The conditioned insufflation gas is then sent to a trocar for injection into a body cavity of a patient.

One of the requirements for delivery of insufflation gas to a patient's body cavity is to maintain the proper flow of insufflation gas into the body cavity. Normally, gas flows from a high-pressure gas source, which is remote from the patient, through an insufflation device and finally into a trocar where the gas is injected into the patient's body cavity. Typically, the insufflation gas is stored in high-pressure containers and a pressure regulator reduces the pressure of the gas to a lower pressure. The low pressure gas is typically delivered to the trocar through an insufflation device containing a set of inline end connectors that couple the source of insufflation gas, the pressure regulator, the filter, the heater, or heater and hydrator to trocar to each other. During the insufflation process the insufflation gas, which is conditioned by filtering, heating and or hydrating before delivery flows through a number of inline end connectors, which are typically connected by flexible tubing.

The conditioned gas is then delivered to the patient through a trocar cannula that extends into the body cavity of a patient. It is known that each of these devices and the connectors for each of these devices between the source of high-pressure insufflation gas and the body cavity of the patient generate what has been considered a negligible fluid resistance.

Typically, during a surgical procedure the amount of insufflation gas injected into the body cavity of the patient, the flow rate of the insufflation gas as well as the velocity of the insufflation gas varies over a wide range. To avoid tissue damage in the patient the flow rate of insufflation gas as well as the gas insufflation pressure in the body cavity as well as other conditions of the insufflation gas need to be controlled.

BRIEF SUMMARY OF THE INVENTION

Briefly, the invention comprises a fluid stabilizer and a medical insufflation apparatus for on-the-go heating and/or hydrating of an insufflation gas during a medical procedure while permitting the use of additional types of insufflation devices without having to connect a different insufflation device to the source of pressurized insufflation gas.

The fluid stabilizer upstream of the gas conditioning trocar as described herein has the benefit of providing for a low resistance gas passage of constant fluid resistance to the insufflation apparatus since the effects of pressure loss through accidentally crimping or bending of the insufflation tubes proximate the trocar are inhibited or eliminated.

A further advantage of the invention described herein is that the fluid stabilizer eliminates or minimizes surface discontinuities often found in conventional inline end connectors since the fluid stabilizer is free of abrupt or discontinuous end line connector surfaces that may increase or exacerbate unrecognized or unanticipated pressure changes in the gas passages that may unknowingly affect the characteristics of the insufflation gas delivered to a body cavity.

A further benefit of the invention is that when the fluid stabilizer comprises a rigid lateral extension, which extends laterally outward from the housing of the trocar, it provides an ergonomic design that enables the fluid stabilizer to comfortably function as a trocar handle, which has the benefit of enabling a surgeon to better control the delicate penetration of the cannula through the body tissue and into the body cavity.

In addition the integral handle also enhances manual control of the trocar as the instruments within the trocar are manipulated during the surgical procedure.

A further feature of the invention is an obturator that can be locked to the trocar to enable the surgeon to better control the penetration of the body tissue covering a body cavity of a patient.

The rigid fluid stabilizer reduces and minimizes the number of inline end connectors required between the trocar and the supply of insufflation gas to thereby limit unrecognized, unexpected and unwanted pressure loses which may unknowingly hamper the ability of the insufflation device to quickly and safely inflate a body cavity.

The fluid stabilizer described herein allows one to eliminate the use of collapsible flexible tubing proximate the trocar and the consequently accidental and unknowingly bending during the surgical procedure, which may abruptly change the internal fluid resistance and flow of insufflation gas through the insufflation device. The bending or crimping has the potential to not only change the flow rates but to introduce other fluid conditions e.g. Such as the "cowanda effect" which may introduce instability or pulses in the gas flow through the insufflation device. In addition, the fluid resistance of the end connectors used to connect the source of the gas to the insufflator may abruptly change since the pressure loss can vary with the flow rate through the insufflator as well as the type of flow within the insufflator.

The insufflation apparatus may be a kit that eliminates or minimizes the changes in gas flow and fluid resistance in the insufflation fluid passages, which are not readily observable or detectable during a surgical procedure but may cause the condition and state of insufflating gas entering the body cavity to change without the knowledge of the surgeon.

The fluid stabilizer through either minimizing or eliminating inline end connectors limits the total fluid resistance between high-pressure source and the body cavity of the patient so as not to adversely limit the flow rate which may make it difficult to maintain the proper insufflation pressure in the body cavity of the patient.

The fluid stabilizer eliminates one of the disadvantages with prior art insufflation devices, namely, that the internal fluid flow resistance of the gas passages, which are upstream of the trocar, may have an unknown adverse effect on the properties of the gas delivered to the patient as well as the rate of delivery of the insufflation gas. For example, the internal fluid resistance of the insufflation device may not only hamper the ability to safely and effectively inflate a body cavity but if collapsible flexible tubing is used for deliver of the gas to the trocar the tubing may be accidentally bent or crimped which can change the properties of the insufflation gas as well as the rate of delivery of the insufflation gas to the body cavity.

While the fluid stabilizer minimizes unseen upstream changes in the properties or condition of the insufflation gas after the gas has been heated and hydrated the incorporation of a heater and hydrator directly into the trocar to form a downstream gas conditioning trocar further minimizes adverse effects in delivery of the conditioned gas to a body cavity as the gas conditioning trocar has the benefit of bringing the insufflation gas to the proper conditions immediately prior to delivery of the gas into the body cavity thus minimize cooling or condensation of moisture in the gas before delivery of the gas to the body cavity.

A further feature of the invention described herein is a cannula connector or adapter having one end attachable to the end of the trocar cannula with the other end of the adapter or cannula connector engageable with a smaller insufflation instrument such as a insufflation needle, for example, a verres needle or the like. The cannula adapter has the benefit of allowing a surgeon the option of beginning the delicate insufflation process using a smaller insufflation needle in conjunction with the trocar. Once the initial insufflation is concluded the surgeon can remove the insufflation needle, quickly detach the cannula connector and insufflation needle from the cannula and insert the cannula of the trocar into the body cavity without having to use an additional insufflation device. The surgical procedure is then performed through an instrument or instruments that can extend through the lumen in the cannula of the trocar.

A further benefit of the invention described herein is that when the fluid stabilizer is used with a double lumen cannula the fluid resistance to the insufflation gas remains constant during manipulating of instruments in the lumen thus allowing the surgeon to smoothly increase, decrease or maintain the insufflation pressure in the body cavity thus inhibiting or preventing tissue damage.

A further advantage is that the fluid stabilizer, the hydration unit and the trocar with an integral housing form a compact easy to use disposable unit.

The use of fixed inline plenum chambers in the flow passages in the fluid stabilizer and the trocar provide for periodic stabilization the insufflation gases during its passage from a supply source to a body cavity.

The elimination or minimizing of inline end connectors can enhance the ability of the insufflation devices ability to quickly inflate a body cavity.

The invention includes the ability to heat insufflation gas immediately prior to injecting the insufflation gas into a body cavity thereby minimizing heat losses after the insufflation gas has been heated.

The invention includes the ability to hydrate the insufflation gas immediately prior to injecting the insufflation gas into a body cavity thereby minimizing condensation after the insufflation gas has been humidified.

The invention enables the use of pressure regulators to maintain the proper insufflation pressure in the body cavity since pressure the effects of pressure loses due to internal resistance of the insufflation apparatus is minimized.

BRIEF DESCRIPTION OF THE DRAWINGS

FIG. 3 is an isolated partial side sectional view of the trocar and an inlet fluid line in fluid stabilized medical insufflation apparatus of FIG. 1;

FIG. 4 is a sectional view of a double lumen insufflation cannula of FIG. 1;

DESCRIPTION OF THE PREFERRED EMBODIMENT

Figure 1:
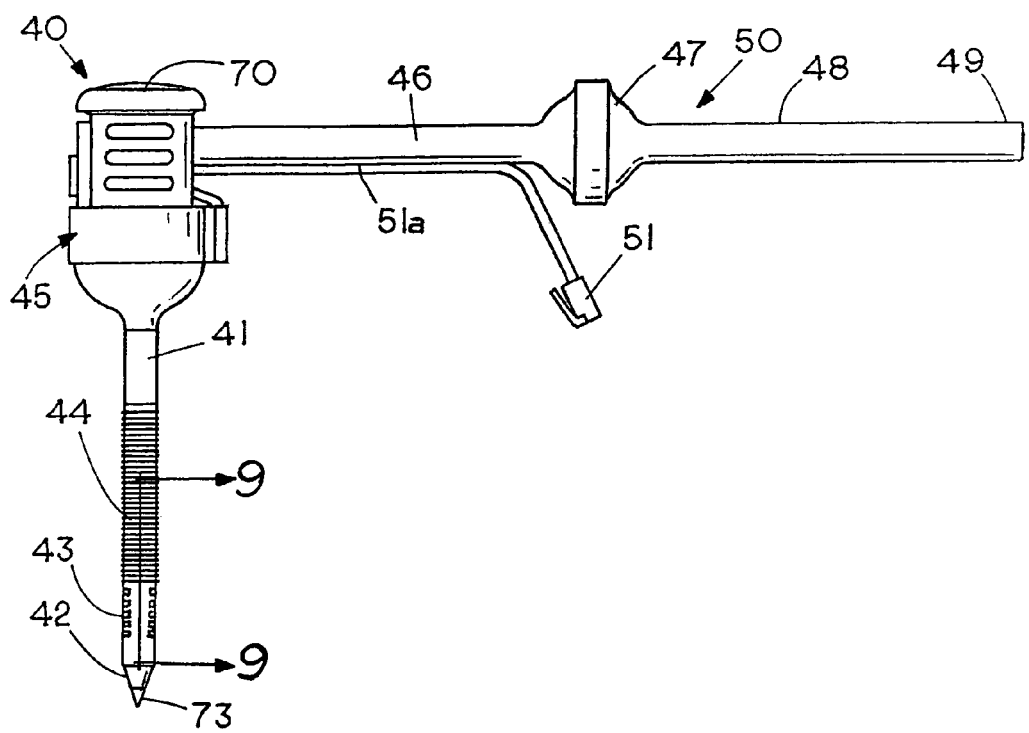
FIG. 1 is a side view of the a fluid stabilized medical insufflation apparatus.
Figure 2:
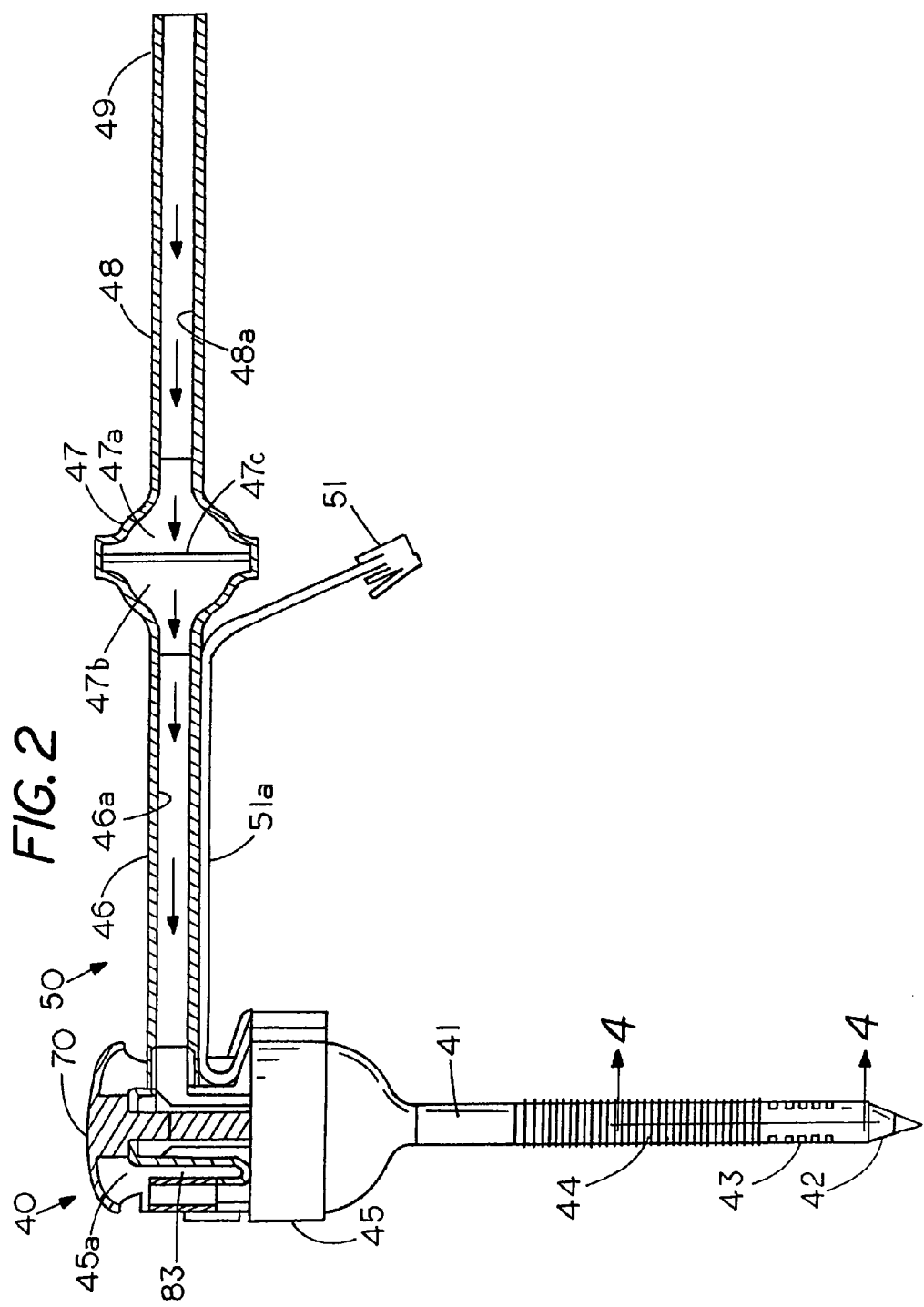
FIG. 2 is a partial side sectional view of the fluid stabilized medical insufflation apparatus of FIG. 1.
Figure 10:
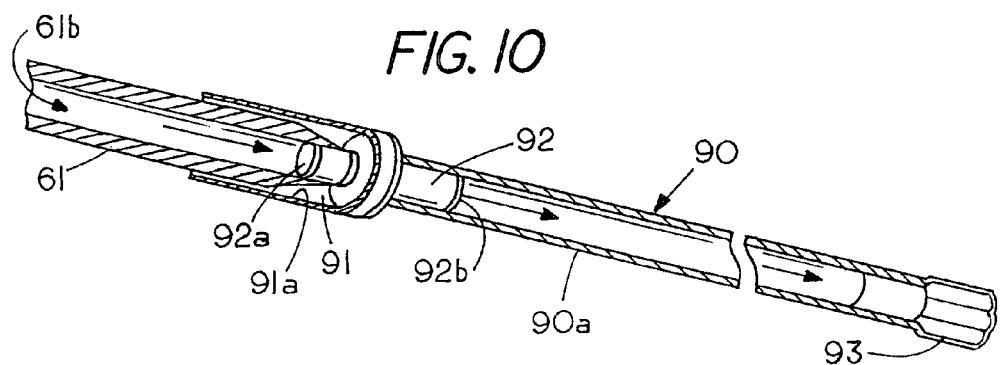
FIG. 10 is a sectional view of the single lumen cannula with a cannula adapter mounted on the end of the cannula.

FIG. 1 is a side view of a medical insufflation apparatus or medical insufflation kit 40 for maintaining a stable fluid flow regime therein during a medical procedure. Insufflation kit 40 may include a cannula adapter 90, such as shown in FIG. 10 for initial coupling an insufflation needle to the cannula. FIG. 1 shows medical insufflation apparatus 40 includes a trocar 45, a fluid stabilizer 50 extending laterally from a central axis of trocar 45. As can be seen in FIG. 2 the fluid stabilizer 50 is free of any gas conditioning apparatus. An obturator 70 is detachably mounted in trocar 45 and may be used for initial piercing of the body tissue. Extending from trocar 45 is an elongated rigid cannula 41 having a tissue-engaging region 44 comprising a series of annular ridges extending along an exterior circumferential portion of the elongated cannula 41. Tissue engaging region 44 may for example comprise a set of circular ridges that project radially outward for frictionally engaging body tissue when the trocar extends through the body tissue proximate the body cavity of a patient. Located proximate the distal end 42 of cannula 41 is a set of fluid injection ports 43 for directing an insufflation gas into a body cavity. Cannula distal end 42 comprises a frusto conically tapered section with a tissue piercing tip 73 of obturator 70 extending outward from the cannula annular distal end 42.

Fluid stabilizer 50 includes a tube 46 having one end rigidly affixed to trocar 45 and the other end rigidly affixed to a downstream side of a rigid inline filter housing 47. Typically, the stabilizer can be affixed to the trocar through solvent bonding or the like although other methods may be used. In the example shown the fluid stabilizer and the trocar housing may comprise either a non rigid or a rigid polymeric plastic tube enabling solvent bonding of the fluid stabilizer to the trocar housing to maintain the flow integrity of the insufflation apparatus before, during and after the insufflation procedure. The opposite upstream side of rigid inline filter housing 47 connects to a inlet tube 48 having an end of the line connector 49 for direct connection to a source of insufflation gas. The source of insufflating gas typically includes a pressure regulator to limit the pressure of the insufflation gas in order to prevent tissue damage to the patient. The present invention through the use of a low resistance fluid passage in the fluid stabilizer allows the pressure in the body cavity to be maintained in a pressure range closer to the set pressure on the regulator since the effects of unstable flow as well as the effects of fluid resistance varying with velocity of the flow therethrough are minimized. One way of reducing the pressure losses in the fluid stabilizer 50 is, to provide an internal fluid passage in the fluid stabilizer that is free of detachable end connectors, i.e. as used herein detachable connectors refers to those end connectors that can be attached and detached such as leur lock connectors, and consequently the surface discontinuities produced by end connectors. As a consequence with a low flow resistance passage in the fluid stabilizer one can safely obtain a faster insufflation time as well as improved transient response times. While the tubing in the fluid stabilizer may be flexible or rigid if the tubing is rigid a further feature of affixing the fluid stabilizer to the trocar is that the fluid stabilizer may be used as a handle to facilitate insertion of the cannula into the body cavity without affecting the condition of the flow threrethrough. When the trocar 45 and the fluid stabilizer 50 are made from a polymer plastic the permanent securement of the fluid stabilizer to the trocar through solvent bonding or the like creates a one-piece insufflation apparatus. The use of a flexible self supporting tubing where the integrity of the tubing side wall is preferably such that bending the tubing does not collapse or restrict the flow passage therethrough may also be used. Thus, the insufflation apparatus described herein inhibits upstream pressure loses therein during a medical procedure.

In the example shown the fluid pathway in the fluid stabilizer includes at least one elongated fluid passage for damping the insufflation gas flowing into the inlet chamber of the trocar to provide a stable low resistance flow regime therein. FIG. 2 shows a multisection cylindrical fluid pathway 46a and 48a extending from an inlet 49 of the fluid stabilizer 50 to a plenum chamber 83 in trocar 45. The fluid pathway, which may be in sections, is characterized by a smoothly configured sidewall free of abrupt surface changes or discontinuities in the sidewall, which may generate fluid perturbations that may introduce unwanted pressure pulses into the body cavity of the patient. A further benefit of the smoothly configured sidewall of the fluid passage described herein is that it enables one to maintain the same or substantially the same fluid resistance under a variety of different flow conditions by minimizing pressure losses that increase with flow changes. In addition to minimizing pressure loses the lower upstream pressure, which is a consequence of the minimization of pressure loses, enhances the ability of the boundary layer in the fluid passages to inhibit or minimize fluid perturbation caused by the sidewalls of the fluid passages to thereby more readily damp fluid disturbances within the system. Thus in one example, the fluid stabilizer allows one to delivery an insufflation gas to the chamber in trocar housing wherein the fluid stabilizer comprises a lateral extension free of pressure reducing inline end connectors affixed to the housing with the housing and the fluid stabilizer each including at least one continuous fluid passage for maintaining a stable low resistance flow regime therein.

An electrical cable 51a, which is partially affixed to the exterior of tube 46, extends from trocar 45 and terminates in a conventional electrical connector 51. Electrical cable 45 includes leads for on-the-go controlling the conditioning of the insufflation gas that enters trocar 45 through a remote control device (not shown).

FIG. 2 shows a partial cross sectional view of insufflation device 40, which is free of inline end connectors, revealing the interior flow path of insufflation gas within the fluid stabilizer 50. Fluid stabilizer 50 includes an elongated fluid entry passage 48a comprising a continuous cylindrical surface for damping and smoothing out the flow of insufflation gas as it directs the insufflation gas (indicated by arrows) into a plenum chamber 47a in filter housing 47. A filter media 47c, for removing unwanted containments from the insufflation gas, separates inline inlet plenum chamber 47a from an inline outlet plenum chamber 47b. In the example shown the low resistance fluid passage comprises a tubular member and the tubular member includes an inline insufflation gas filter 47c therein with the fluid stabilizer free of gas conditioning means. The upstream plenum chambers 47a provides a zone where the velocity of the insufflation gas exiting the passage 48a decreases while the downstream plenum chamber 47b, which is located on the other side of filter media 47c, provides a zone of low velocity insufflation gas velocity prior to the insufflation gas entering elongated fluid passage 46a. Plenum chamber 47b connects to an intermediate cylindrical fluid passage 46a with fluid passage 46a having a continuous elongated cylindrical surface for further damping and smoothing the flow of insufflation gas therein prior to delivery of the insufflation gas to an annular plenum chamber 83 located in trocar 45. The length of the fluid passages are such that irregularities and instabilities in the flow of insufflation gas through the connector or the filter media can be dampened by the boundary layer viscous forces acting on the flowing insufflation gas to thereby maintain a stable fluid regime within the fluid stabilizer during operation of the insufflation apparatus.

The affixing of the fluid stabilizer 50 and the trocar 45 to each other in a fixed link provides a fixed low resistance fluid path, which is free of inline connectors between inlet 49 and trocar plenum chamber 83. Having the flow passage free of internal abrupt or discontinuous fluid surfaces, which are found in conventional inline end connectors such as Leur connectors, not only causes fluid resistance but may cause fluid flow instability. Fluid stabilizer 50 can minimize or eliminate the inline connector losses since the fluid stabilizer is free of conventional in line end connectors, which provide tortuous fluid paths therethrough. To prevent crimping or bending the tubing in the fluid stabilizer preferably should have self-supporting walls that resist collapsing if the tubing is bent. Tubing with self-supporting walls that resist collapsing when bent is commercially available. An example of such tubing is a PVC medical grade USP Class VI tubing having a hardness of 70 on the Shore A scale. Preferably tubing with a circular cylindrical passage therein may be used, however, other shape passages that provide low resistance may also be used. A benefit of the stabilizer having a set of rigid tubes with fixed fluid surfaces is if the tube cannot bend or flex it eliminates changes in fluid resistance which may occur during handling or manipulating of the trocar. To further decrease inline pressure losses a control valve or shut off valve for the insufflation apparatus 40 may be located upstream of the connector 49 thus ensuring that the pressure losses due to internal fluid resistance remains the same for each insufflation apparatus, which eliminates a pressure tuning of the pressure regulator in response to use of a different insufflation apparatus should the insufflation apparatus need to be changed. In operation connector 49 may be connected directly to the source of pressurized insufflation gas thereby minimizing inline pressure losses. As can be seen in FIG. 2 the flow passages in fluid stabilizer 50 and trocar housing are free of abrupt surface protrusions or abrupt changes in the fluid passageway that may cause fluid pressure loses as well as fluid instabilities. Thus, a feature of the invention is that fluid perturbations, which may be unknown or unappreciated, are minimized or eliminated through use of the fluid stabilizer and the trocar described herein. In addition the elongated passages upstream and downstream of the filter media generate a more stable boundary layer that dampens the insufflation gas as it enters the trocar housing thereby enhancing the ability of the insufflation apparatus to smoothly deliver insufflation gas both at high and low flow rates to the body cavity of a patient. While different lengths of the elongated passages in the fluid stabilizer may be used depending on the particular application to obtain the benefits of the invention FIG. 2 shows the length of the elongated passages in the fluid stabilizer as long as or greater in length than the fluid passages in trocar 45 which is affixed to the fluid stabilizer.

FIG. 2 also illustrates an inline plenum chamber 47a located upstream of the filter media 47c and a further inline plenum chamber 47b located downstream of filter media 47c with the plenum chambers providing inline regions of lower velocity insufflation gas to provide for periodic velocity stabilization of the insufflation gases. Similarly, FIG. 3 shows the medical insufflation apparatus 40 includes a downstream inline plenum chamber 83 and a downstream inline plenum chamber 84 with insufflation gas directed through at least four inline plenum chambers prior to delivery to the body cavity.

FIG. 3 shows a sectional view of a portion of the junction of the trocar 45 and the fluid stabilizer 50 with the low resistance 46 tube having an interior smoothly contoured sidewall passage 46a with a lumen 46b therein. Elongated tube 46 is affixed to rigid housing inlet 45b with inlet 45b also having a smoothly contoured sidewall 45a therein that smoothly mates with fluid passage sidewall 46a. Inlet 45b connects to housing 45c, which includes an annular plenum chamber 83 formed by housing 45c and inner cylindrical cannula member 42. The arrows in FIG. 3 illustrate the direction of the flow of insufflation fluid in lumen 46b followed by the annular flow of insufflation fluid of gas into annular plenum chamber 83. The insufflation fluid in annular plenum chamber 83 flows through a conditioning media 20 and into a lower annular plenum chamber 84, which directs the conditioned insufflation fluid into the annular lumen 44a formed by cannula outer tube 41 and cannula inner tube 42. In the example shown a resealable charging port 59 connects to extension 45d in trocar 45 to permit charging the conditioning media 20 prior to initiating of the medical procedure or on-the-go charging during the medical procedure. Charging may be done in any of a number of ways including periodic injections of hydrating fluid into port 59 through a syringe or the like.

FIG. 3 illustrates the inline plenum chamber 83 located upstream of the conditioning media 20 and the further inline plenum chamber 84 located downstream of conditioning media 20 with the plenum chambers providing inline regions of lower velocity insufflation gas. The inline regions of low velocity insufflation gas provide for periodic velocity stabilization or calming of the insufflation gases. Consequently, a series of inline multiple plenum chambers in the fluid stabilizer and the trocar 45 may help to stabilize the flow of insufflation gas during the periods where the flow rate changes due to changes in insufflation pressure in a body cavity.

FIG. 4 shows an isolated section view of the distal end of the double lumen cannula comprising an outer tube 41 and an inner tube 42 with the annular insufflation passage 44a therebetween. In operation the insufflation fluid flows through the annular passage 44a and is directed radially outward through fluid injection ports 43. The fluid injection ports may be the non jet streaming type of fluid injection ports described in Douglas Ott U.S. Pat. No. 6,733,479 which is herby incorporated by reference. Extending along the exterior surface of cannula is a set of annular tissue engaging ridges or radial protrusions 44 that can assist in holding the trocar cannula in engagement with the body tissue during a medical insufflation procedure.

Figure 5:
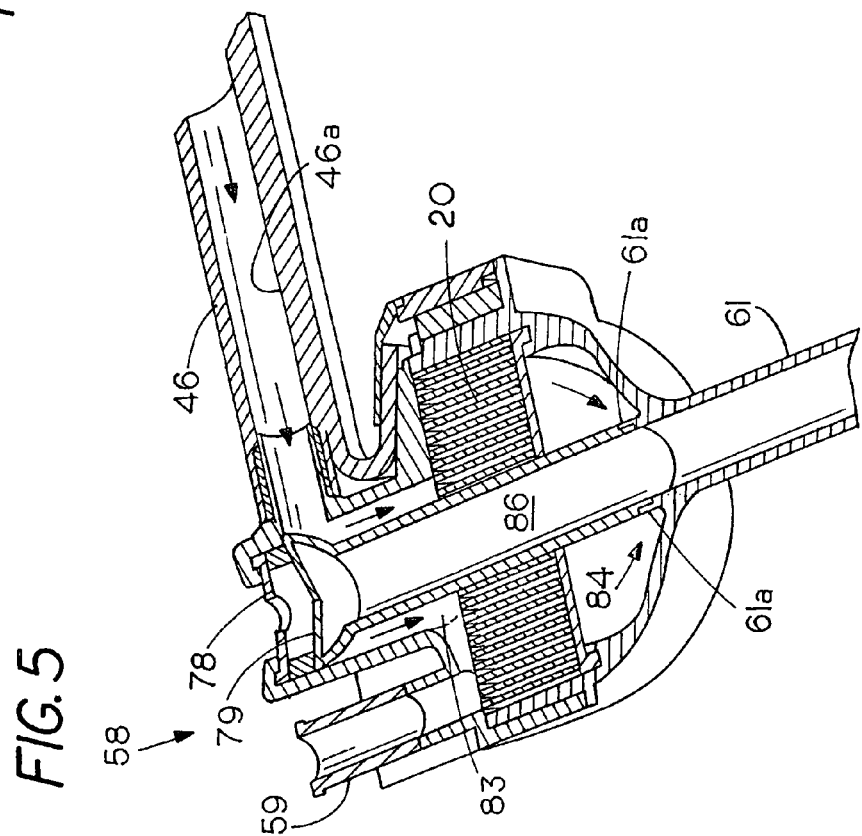
FIG. 5 is partial side sectional view of single lumen trocar and an inlet fluid line in fluid stabilized medical insufflation apparatus.

FIG. 5 shows an example of a insufflation apparatus 58 having a gas conditioning trocar with a single lumen cannula 61 for delivery of insufflation gas as well as for insertion and manipulation of instruments therein. Identical components in insufflation apparatus 58 and insufflation apparatus 40 have identical numbers. In operation of the insufflation apparatus 58 the insufflation gas flows through elongated cylindrical passage 46a and into annular plenum chamber 83, through the gas conditioning media 20 and into the annular plenum chamber 84. From plenum chamber 84 the conditioned insufflation gas flows through ports 61a and enters lumen 86 where it flows through cannula 61 and into the body cavity of a patient though either the end of the cannula or ports on the side of the cannula. In this example the instruments and the insufflation gas share the same fluid passage 86 in the trocar cannula.

Figure 6:
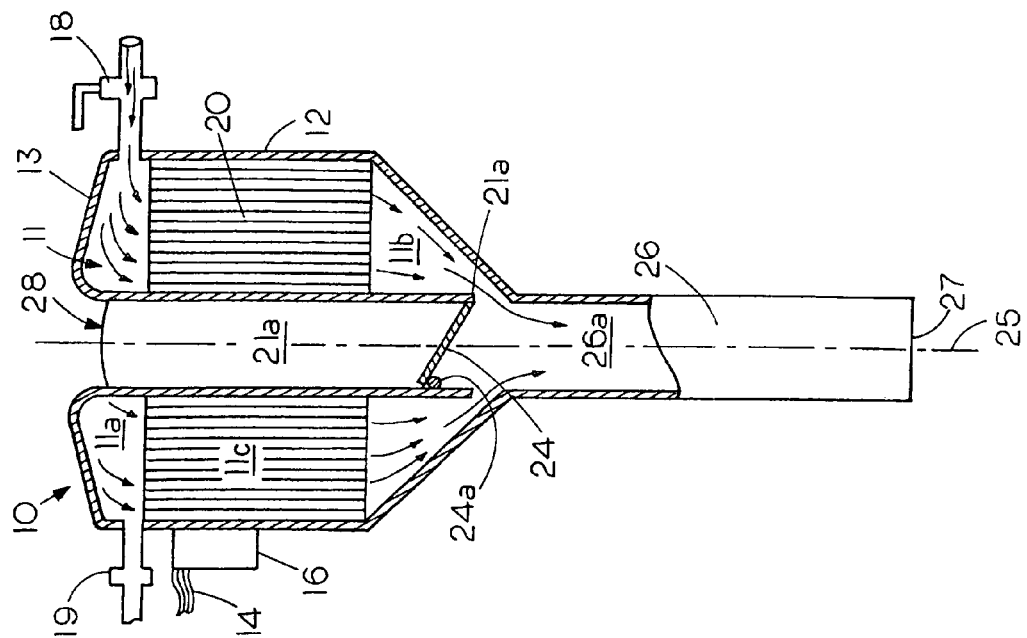
FIG. 6 is a side view of a gas conditioning trocar with a single lumen.

FIG. 6 shows a partial cut away side view of another example of a single lumen gas conditioning trocar 10 for on-the-go heating and/or hydrating of an insufflation gas during a medical procedure. Gas conditioning trocar 10 may be used independent of the fluid stabilizer or incorporated with or into the insufflation apparatus described herein. Trocar 10 includes a cylindrical housing 12 having a cannula 26 on one end and a cover 13 on the opposite end. The cannula 26 comprises an elongated cylindrical tube for extending into a patient's body cavity. While not explicitly shown, cannula 26 may include a sharp member for piercing the skin and tissue between the skin and the peritoneal cavity. Such a member may be spring loaded and may take many different forms as understood by persons skilled in the art. Any form of a sharp member may be used or the sharp member omitted without departing from the scope of the invention.

Cylindrical housing 12 and an upper coaxial tube 21 form an annular chamber 11 within trocar 10. Chamber 11 could have another shape without departing from the scope of the invention. Annular chamber 11 comprises three parts, an upper annular plenum chamber 11a where insufflation fluids and insufflation gas are introduced, a central annular chamber 11c, which may contain a conditioning media 20 for transporting the insufflation gas and/or a hydration fluid threrethrough while bringing the insufflation gas to a conditioned state as it enters the lower annular plenum chamber 11b. From plenum chamber 11b the conditioned insufflation gas flows into cannula 26 through an annular outlet port 21a. A feature of the spiral configuration of the conditioned media, which has an end in the plenum chamber 83 as shown in FIG. 3, is that the conditioning media functions as a flow straightener for delivery of the conditioned insufflation gas to annular chamber 44a.

Connected to one side of housing 12 may be a valve 18 for controlling the flow of insufflation gas into upper annular plenum chamber 11a and similarly connected to the opposite side of housing 12 may be a further valve 19, which may be a check valve, to control the flow of hydration fluids into housing 12 as well as to prevent backflow of hydration fluids. While mechanical valves are shown other types of controls may be used; for example, fluidic controls may be used to control the delivery of fluids to the gas conditioning trocar. Either valve 19 or valve 18 or both may be omitted without departing from the scope of the invention. For example, valve 18 may be replaced by a fluid stabilizer or the trocars may have multiple ports into housing 12 where flow of gases and fluids into such ports is controlled by valves in tubing leading to such ports. In the embodiment shown, junction box 16 is mounted on the side of housing 12 and contains electrical leads 14 from a heater located in the conditioning media 20. Junction box 16 can be omitted without departing from the scope of the invention. In some embodiments, the heater may be omitted. In other embodiments, conditioning media 20 may be omitted. Typically, the hydration fluid may be water, however, other fluids may be included in addition to or instead of the water. For example, a saline solution, an anesthetic, an antibiotic, or other pharmacologic agent could be used.

As used herein, the term "agent" means any organic substance, inorganic substance, inert or biologically active substance of pharmacologic material, that may effect or enhance tissue healing, reduce infection, reduce adhesions formation, modify the immunologic response, treat specific disease processes, reduce pain or be used for any therapeutic or diagnostic purpose. This includes materials in solid, liquid or gas phase, and materials that are water (aqueous) based, colloid and non-colloid suspensions, mixtures, solutions, hydrogels, lypholized materials, hydrophobic, hydrophilic, anionic, cationic, surface active agents, surgical adjuvants, anticoagulants, antibiotics, immunologic stimulators, immunologic suppressants, growth inhibitors, growth stimulators, diagnostic materials, anesthetic agents, analgesic agents, and materials by themselves or dissolved or based in other materials, such as, but not limited to, alcohols, ethers, esters, lipids and solvents. The agent can be dry, such as in a powder form. Any material that can be carried by the flow of gas into a body cavity or onto a surface for therapeutic or diagnostic purposes can be delivered in accordance with this invention. It is not intended to limit the present invention to the above examples of agents. Furthermore, the gas stream may be treated with any type or combination of agents in accordance with the present invention. An example is to treat the gas stream with a humidifying solution for hydration to prevent desiccation, an antibiotic to reduce infection, an anti-inflammatory to reduce inflammation and an anti-adhesive to reduce adhesions and improve healing. Agents such as those sold under the trademarks Adept manufactured by ML Laboratories, Adcon manufactured by Gliatech and Atrisol manufactured by Atrix Laboratories can be used to reduce adhesions.

While in this embodiment, hydration fluids enter through valve 19, the trocar could be packaged in a precharged condition with fluid contained in chamber 11c. A recharge port could also be included in tubing leading to the trocar or placed anywhere on the trocar body such that a fluid can reach chamber 11c.

In the illustrated embodiment of FIG. 6, conditioning media contains both a heater and a porous material capable of absorbing water. In operation of this embodiment of gas conditioning trocar 10, the insufflation gas and the hydration fluids are introduced into plenum chamber 11a and flow in an axial direction through the conditioning media 20 in chamber 11c where the insufflation gas may be hydrated and heated to a temperature near body temperature for injection into the body cavity of a patient. As the insufflation gas and hydration fluids flow through the conditioning media 20, the conditioning media 20 allows the insufflation gas to be hydrated and/or heated immediately prior to injection of the insufflation gas into the body cavity of a patient thus avoiding transport loses that may occur with remote hydration units. A portion of cannula 26 is typically inserted into a body cavity.

The conditioned insufflation gas flows from lower plenum chamber 11b into passage 26 through annular inlet port 21a. A surgical instrument may be passed through instrument inlet 28, into passage 21a and, through cannula 26 and out the end 27 of cannula 26. The instrument may be withdrawn and other instruments may be used in a similar fashion throughout the procedure. As such, the delivery of conditioned insufflation gas and the use of surgical instruments may occur simultaneously without adversely affecting or interfering with each other.

In some embodiments, the insufflation gas may only be hydrated and the heater in conditioning media can be omitted. In other embodiments, the insufflation gas may only be heated and the conditioning media 20 may be omitted. In other embodiments, a material capable of filtering insufflation gas may be used as conditioning media 20 with or without a heater. Thus, the invention further includes a trocar 10 with only an insufflation gas filter in cavity 11c.

Figure 7:
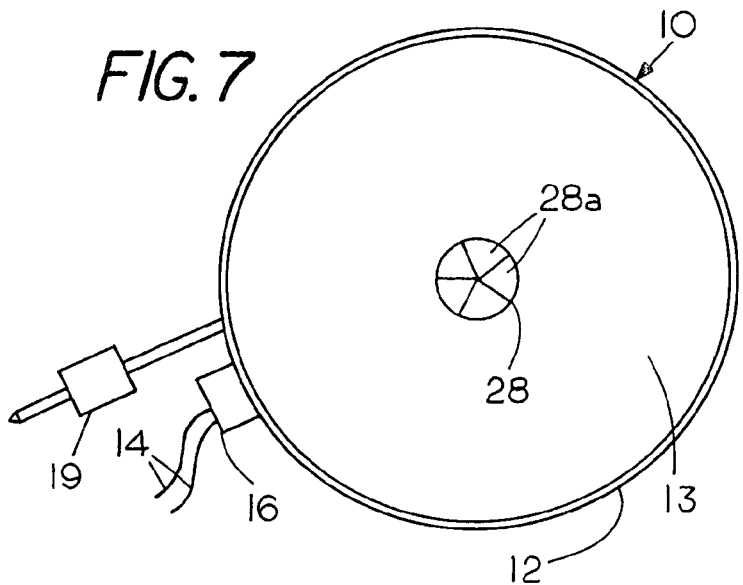
FIG. 7 is top view of the gas conditioning trocar of FIG. 6.

FIG. 7 shows a top view of the trocar housing 12 revealing an inlet instrument port 28, which is located in the center of housing 12. In this embodiment, extending across instrument port 28 is a closure comprising a plurality of segment shaped resilient flaps 28a that normally extend radially inward in tube 21 to block passage 21a and thereby inhibit or prevent backflow of insufflation gas therepast whether or not a surgical instrument is present in trocar 10. The closure may comprise a duckbill opening or lever valve. When a surgical instrument is inserted into trocar 10 the flaps 28a flex to allow the instrument to enter and pass through passage 21a in tube 21. Preferably, the flaps 28a are made of a resilient material such that they form a gas seal around the exterior surface of the surgical instrument therein to inhibit or prevent insufflation gas from escaping therepast when the surgical instrument is located in trocar 10. If the surgical instrument is withdrawn from tube 21, then the flaps 28a return to the closed condition shown in FIG. 6 to inhibit or prevent insufflation gas (e.g., conditioned gas) from escaping through instrument inlet port 28. A further benefit is that the flaps 28a may prevent contaminants from inadvertently entering trocar 10. While resilient flaps are shown comprising the closure other methods and means may be used to close off the instrument port to inhibit or prevent backflow of insufflation gas therepast. Any technique for doing so may be used without departing from the scope of the invention.

In the example shown the on-the-go and in situ heating and hydrating of the insufflation gas takes place in conditioning media 20 which is located in the annular chamber in the gas conditioning trocar 10.

Figure 8:
FIG. 8 is a side view of a multilayer media in an unwound condition.

FIG. 8 shows a side view of an example of a strip of a conditioning media 20 for bringing an insufflation gas into a conditioned state. Media 20 comprises multiple layers i.e. a multilayer media, in an unwound or unassembled condition. In the example shown the materials of multilayer media 20 include a layer of gas transfer material comprising netting 32 and a layer of a fluid transferring material comprising hydrophilic material 30 with a heater assembly 34 extending therebetween. Heater assembly 34 includes a temperature sensor 22 on one end and a pair of electrical leads 14 on the opposite end for connection to a power source. Although three layers are shown the number and composition of the layers of material as well as the thickness of the layers may be modified according to the specific application. Temperature sensor 22 may be part of heater assembly 34 or may be separately mounted in trocar 20 to monitor the temperature of the heater or of the insufflation gas before the insufflation gas is discharged from the trocar 20. Additional temperature sensors 22 may be included and control circuitry to control the heater such that the insufflation gas temperature is maintained within a temperature range may be located within junction box 16 or remotely from the heater assembly 34 and temperature sensors.

One or all of the above components can be omitted from conditioning media without departing from the scope of the invention. As noted above, some embodiments may have a filtering media, some may omit the heater, and some may include only a heater and no other media. Any arrangement of the heater, temperature sensor and absorbent material may be used without departing from the scope of the invention. The media may be arranged to allow gas to primarily flow over or primarily flow through the media. The heater may be located in chamber 11c or in any other chamber of trocar 10 where the insufflation gas can be treated. Preferably, the gas will be heated substantially simultaneously as shown but could be heated and humidified separately.

Figure 9:
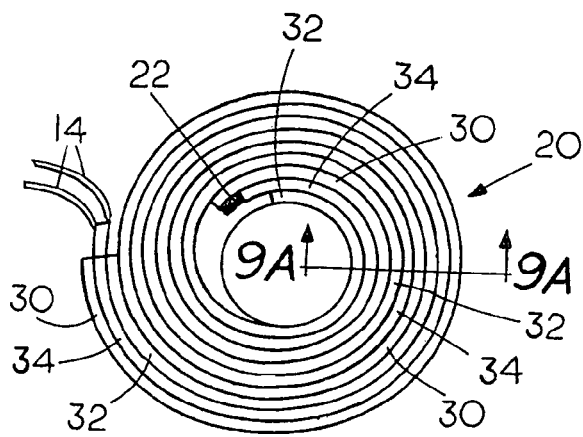
FIG. 9 is top view of the multilayer media arranged in a spiral configuration.

FIG. 8 shows the example strip of multilayer media 20 comprises a plurality of three layers of materials 30, 32 and 34 which may be wound into a spiral configuration that may be inserted into the annular chamber in trocar 10. In the spiral configuration state, as shown in FIG. 9, the hydrating liquid may be brought into proximity of a heater assembly 34 through an absorbing action of a hydrophilic layer 30 in media 20. The absorbing action allows distribution of the hydrating liquid proximate the heater assembly 34. Similarly, a porous netting 32 may allow the insufflation gas to flow thrrethrough so the gas can be brought into proximity of the heater assembly 34 to enable the insufflation gas to be brought to a conditioned state.

Figure 9A:
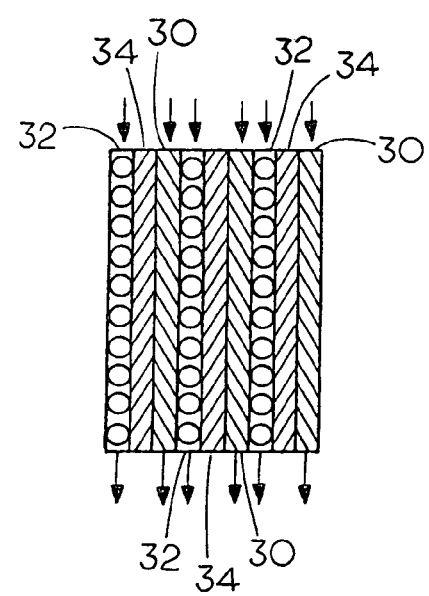
FIG. 9A is a cross sectional view taken along lines 9A-9A of FIG. 9.

FIG. 9A is a cross sectional view of the spirally wound media 20 taken along lines 9A-9A of FIG. 9 revealing the multiple layers comprising the conditioned media 20.

In order to secure the multilayer media 20 in the housing 12 the multilayer media 20 may be wound into a diameter slightly larger than the diameter of housing 12 to enable one to friction fit multilayer media 20 in housing 12. If frictional forces are used to hold multilayer media 20, then the multilayer media should be selected to offer sufficiently low flow resistance so that the insufflation gas flow flowing thereto will not displace the multilayer media 20.

Alternatively, multilayer media 20 could be adhesively secured to housing 12. It is noted that an advantage of the friction fit of multilayer media 20 in housing 12 is that the friction fit reduces the need for an adhesive to hold multilayer media 20 in place. An adhesive may interfere with the flow of insufflation gas from one layer of multilayer media 20 to another. An alternate method of holding the multilayer media 20 in position may be to use a radial supports in chamber 11b to support the lower end of multilayer media 20. Other methods of securing the multilayer media 20 may also be used to maintain the multilayer media 20 in position to deliver hydrated insufflation gas to annular outlet port 21a.

To decrease the pressure drop through netting 32 two or more layers of netting may be placed proximate to each other to increase the porosity though the netting. That is, netting 32 provides flow passages for the insufflation gas to flow from plenum chamber 11a to plenum chamber 11b without undue but sufficient resistance so that the hydration fluid and the hydration gas can be maintained in proximity to enable hydration to take place in embodiments where hydration is performed. A suitable netting 32, for example, is a bi-planar polypropylene netting having properties including a density of 11 strands per inch and a thickness of 0.030 inches (e.g., Delstar, Middleton, Del.). Any netting capable of allowing gas flow could be used without departing from the scope of the invention. Also, the netting 32 could be omitted.

Multilayer media 20 may include at least one layer of a liquid transfer media, which for example may be a hydrophilic media 30, that readily absorbs and retains a volume of hydration fluid provided to plenum chamber 11a. While other types of materials, for example wicking materials, may be used to deliver the hydration fluid into proximity of the heater assembly 34, the hydrophilic media 30 may bring the hydration fluid in close proximity to both heater assembly 34 and the insufflation gas through an absorbing action. Similarly, two or more layers of hydrophilic material may be used to bring the hydration liquid proximate the heater assembly.

Hydrophilic media 30 may be thin and flexible so that it is easily wound in a spiral configuration with the other layers of multilayer media 20 as shown in FIG. 4. Although many types of hydrophilic material are useable, a typical suitable hydrophilic media 30 is cellulose which is commercially available from Knowlton, Watertown, N.Y. having the following characteristics: a basis weight of 91-99 pounds/3000 ft$^2$ and a thickness of about 0.028-0.034 inches.

The multilayer media 20 may include a heater assembly 34, which may comprise an elongated flexible heating element that has external electrical leads 44 for connecting to a source of electrical power. The heater assembly 34 may be thin and flexible such that when it is sandwiched between the hydrophilic layer 30 and the layer of netting 32 the combination can be wound into a spiral configuration that can be inserted within housing 12. An advantage of the spiraled configuration is that it provides a continuous extended area for heating and hydration of the insufflation gas, i.e., the insufflation flow path is long. In the preferred embodiment, heater assembly 34, for example, is a resistance heating element made of etched copper foil coated with a layer of polyimide. Another layer of polyimide may coat the foil surface. The coating of polyimide reduces the likelihood of heater assembly 34 from contacting the hydration fluid or hydrated gas such that an electrical short results. As discussed above, however, any type of heater and any type of absorbent material may be used with the invention.

One end of heater assembly 34 may terminate with a temperature sensor 22 for measuring the temperature of the heater in the gas conditioning trocar 10. In other embodiments, multiple temperature sensors may be used and may be located elsewhere to sense the temperature of the gas directly rather than sensing the temperature of the heater. The temperature sensor can be located in one of the chambers 11b or 11c or located in the cannula 26. In some cases, a remote sensor (e.g. an electronic infrared sensor) exterior to the trocar could be used. When heater assembly 34 is layered with the other materials of multilayer media 20 and friction fit into housing 12, temperature sensor 22, for example a thermistor, detects the temperature of the heater at lower plenum chamber 11b. A heater control, not shown, can increase or decrease the power supplied to heater assembly 34 to maintain the temperature within a desirable range for injection into a body cavity. The opposite end of heater assembly 34 may terminate with electrical leads 14 which can be connected to a power source. When heater assembly 34 is layered with netting 32 and hydrophilic media 30 and assembled into a spiral configuration, electrical leads 14 may extend beyond the multilayer media 20. Thus, when the multilayer media 20 is placed in housing 12, the electrical leads 14 may extend beyond housing 12 for connection to a source of electrical power as shown in FIG. 6.

In the preferred embodiment, multilayer media 20 is assembled into a spiral configuration (FIG. 9) although other configurations may be used. An advantage of the spiral configuration is that the hydrating fluid and insufflation gas are brought in to close proximity to the heater assembly 34 as they flow from annular plenum chamber 11a to annular plenum chamber 11b. Although an annular conditioning media 20 which extends from side to side is shown, the gas conditioning media may take other shapes or forms which allow the insufflation gas to be conditioned within the trocar. For example, only a portion of the annular chamber in the trocar may be used for the conditioning of the gas. A further benefit and advantage of use of a multilayer media is that multilayer media 20 can more easily be assembled in a flat condition and subsequently wound into a spiral configuration for insertion into the annular chamber of the trocar 10.

Referring to FIG. 6, an elongated cylindrical passages 21a and 26a extend along a central axis 25 of trocar 10. Passages 21a and 26a are of adequate diameter to simultaneously house a surgical instrument and allow a flow insufflation gas without undue fluid resistance thereto.

Trocar 10 may include a closure such as a hinged flap 24, which is normally held in a closed position by a spring 24a to prevent backflow of bodily fluids or other materials from the patient's body cavity. Other closures such as a duckbill connector may be used. Flap 24 opens in response to a medical instrument being inserted into passages 26a. It is noted that while flap 24 is the preferred embodiment, other methods or structures may be used to prevent backflow.

FIG. 10 shows a sectional view of cannula adapter 90 attached to a single lumen cannula 61. In the example shown the insufflation adapter 90 is frictionally mounted on the distal end of cannula 61 with a fluid seal formed between the engaging surfaces of the cannula adapter and the cannula 61. Insufflation adapter 90 allows one to use the insufflation apparatus 40 in different insufflation modes. In one mode the cannula 61 directs the insufflation gas directly into the body cavity through side ports on the cannula. In another mode the cannula directs the insufflation gas into the body cavity through the port or ports on an insufflation needle, which is temporarily attached to the cannula through cannula adapter 90.

FIG. 10 shows a sectional view of the cannula adapter 90 comprising an elongated tube 90a having a first end with an annular member or sleeve 91 that fits over the distal end of the cannula 61 and a second end having a sleeve or connector 93 for forming sealing attachment to an insufflation needle or the like. Located partially in one end of adapter 90 is a hollow plug 92 having one end extending into tube 90a and the other end into the distal end of cannula 61. The outside cylindrical surface of portion of plug 62, which extends into tube 90a, forms a fluid seal between adapter 90a and cannula 61. Plug 92 may be made from a resilient material to enable the resilience of the plug to form a pressure seal although other methods of sealing plug 92 to tube 90a may be used. The plug 92 includes a fluid passage 92a extending threrethrough that allows insufflation gas to flow from cannula lumen 61b into adapter 90 and from there to an insufflation needle or the like attached thereto. The arrows indicate the direction of flow through the cannula 61, the plug 92 and the cannula adapter 90.

To prevent leakage of insufflation fluids the outside diameter of the plug 92 is such that it forms a snug fit with the cylindrical interior surfaces of cannula 61. If the cannula includes side ports for introduction of insufflation gas the annular sleeve 91 is of sufficient length to cover the side ports on the cannula to prevent flow therepast. To prevent leakage of fluid from the side ports of the cannula annular sleeve 61 the adapter sleeve 91a should form a snug fit with the outer surface of the cannula 61. If desired a resilient material may be included on the inside surface of annular sleeve 91 with the interior surface of sleeve 91 forming a slight interference fit with the outside surface of the cannula 61. As an alternate sleeve 91 may be made from a resilient material to allow a snug leak proof connection to be formed with the distal end of the cannula. Thus the adapter 90 allows one to seal lateral ports on the cannula to prevent flow threrethrough when the cannula adapter 90 is in use.

The distal end of adapter 90 includes a fitting 93 suitable for attachment to conventional insufflation needles, for example a verres needle. Fitting 93 may comprise a Leur fitting or the like to enable coupling with existing insufflation needles. With the insufflation apparatus 40 as described herein one has the option of using either an insufflation needle, which is smaller than the trocar, to initiate insufflation and when the initial needle insufflation stage is achieved one can convert from needle insufflation to trocar insufflation by merely removing the adapter 90 and the insufflation needle from the end of cannula 61. The cannula 61 can then be used for direct insufflation of the body cavity of a patient. Thus the adapter eliminates the need for an entire separate insufflation apparatus for both trocar insufflation and needle insufflation needle since the same trocar insufflation apparatus can be used with needle insufflation.

Figure 11:
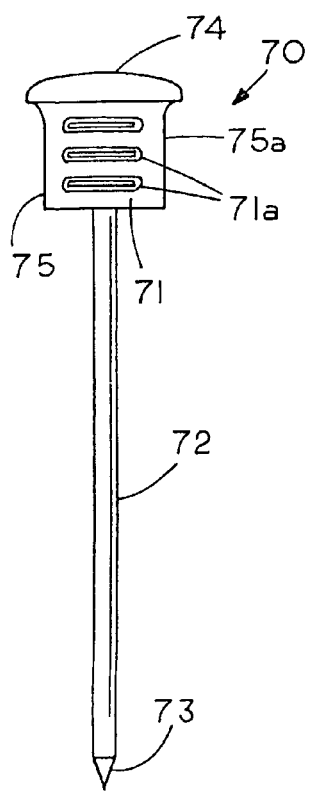
FIG. 11 is an isolated side view of the obturator of FIG. 1.
Figure 12:
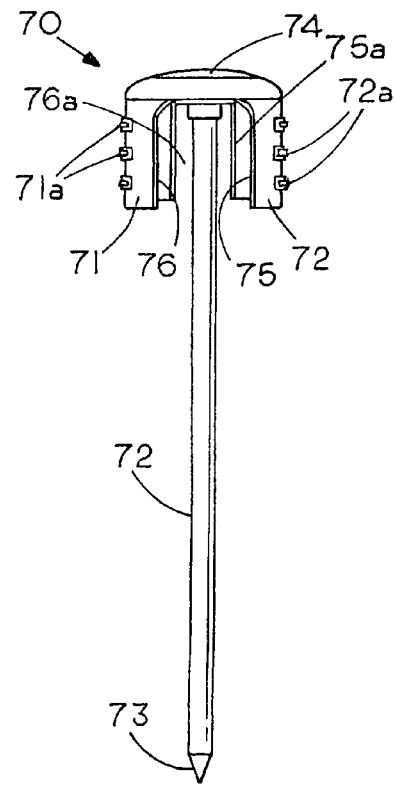
FIG. 12 is an isolated front view of the obturator of FIG. 1.

FIG. 11 is an isolated side view of the obturator of FIG. 1 for using with the insufflation apparatus 40. FIG. 12 shows a side view of the obturator of FIG. 11 rotated 90 degrees from the view shown in FIG. 11. Obturator 70 includes a domed head 74 with a first set of lateral edges 75 and 75a and a second set of lateral edges 76 and 76a for locking the obturator to the housing of trocar 45. A set of ridges 71a on the side of obturator and a set of ridges 72a on the opposite side of obturator provide for a higher coefficient of friction for enhanced gripping. The cylindrical shaft of the obturator 72 terminates in a conical point 73 for insertion through the body tissue of a patient. Conical point may include a surface coating of a low friction resistance material, for example polytetrafluoroethylene, which minimizes resistance to piercing of the fascia body tissue with the conical point 73.

The inclusion of the obturator with the adapter provides an insufflation kit wherein the tissue piercing and the insufflation can be achieved with either of two different insufflation modes without having to use separate insufflation apparatus for each mode.

Figure 13:
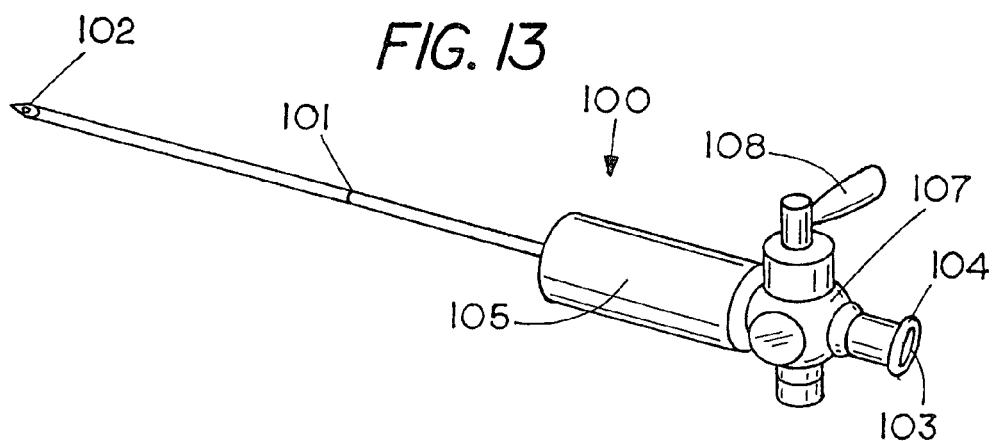
FIG. 13 is a perspective view of an insufflation needle.

FIG. 13 shows an example of a typical insufflation needle 100 for initial delivery of an insufflation gas to a body cavity. Insufflation needle 100 contains an elongated tube 101 with a pointed end 102 for piercing through body tissue and into a body cavity to enable one to begin the process of insufflating a body cavity. A housing 105 for grasping and manipulating the insufflation needle 100 supports one end of the elongated tube 101 and a valve 107 having a handle 105 to open and close the fluid path 103 through the tube 101, which extends from the other end of the housing 105. A fluid connector 104 extends from valve 107 to permit attachment of the insufflation needle 100 directly or indirectly to the cannula adapter 90 of FIG. 10. Connection to adapter 90 may be made through frictional engagement of connector 104 with connector 93 although other types of connections may be used for example, threaded or locking connectors.

Figure 14:
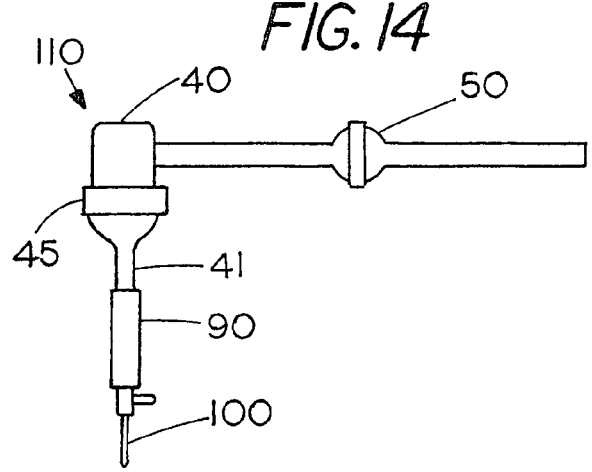
FIG. 14 is a front view of the medical apparatus of insufflation kit in an assembled condition for needle inflation.

FIG. 14 shows components of an insufflation kit 110 in an assembled ready to use state. In the assembled condition the fluid stabilizer 50 extends laterally from trocar 45 and the cannula adapter 90 connects to the cannula 41 of the trocar 45. The insufflation needle 100 extends outward from the adapter 90 to enable one to insufflating a body cavity from the insufflation gas delivered to fluid stabilizer 50. In this example the obturator 70 has been removed since an inflation needle will be used to imitate the tissue piercing proximate the body cavity.

Insufflation kit 110 enables a user to insufflate a body cavity through either an insufflation needle or a trocar as well as to make an on-the-go change between an insufflation needle and a trocar. For example, insufflation needle 100 may be used for initial insufflation of the body cavity. When one needs to use the trocar to contain the instruments and maintain insufflation one can merely disconnect and remove the insufflation needle 100 and cannula adapter 90 from the cannula 41. One can then insert cannula 41 directly into the body cavity without having to replace the fluid stabilizer 50 or the gas-conditioning trocar 40, which was connected to an end of cannula adapter 90. Not only can time be saved but the use of separate insufflation apparatus for both the insufflation needle and the trocar is eliminated since the same fluid stabilizer and trocar can be used with trocar insufflation as well as needle insufflation since separate sterilizing or resterilization will not be required.

In the example shown all of the components of insufflation kit may be rigidly connected to each other so that the insufflation apparatus 110 can be manipulated as a unit. In other cases only some of the components may be rigidly connected, for example one may want the insufflation needle to be separately manipulated from the trocar through use of a flexing tubing in the cannula adapter.

We claim:

1. A method of injecting insufflation gas into a body cavity during a medical surgical procedure to reduce unwanted upstream pressure losses and fluid instabilities that hamper the ability of the insufflation device to quickly and safely insufflate the body cavity including the steps of:
   extending a trocar cannula into a body cavity;
   flowing the insufflation gas into a trocar and the trocar cannula through a fluid stabilizer free of inline end connectors with the fluid stabilizer having in series a first smoothly contoured elongated sidewall passage to dampen the flow of insufflation gas flowing therethrough, a first plenum chamber located downstream of the first smoothly contoured elongated sidewall passage, a filter media located downstream of the first plenum chamber, a second plenum chamber located downstream of the filter media and a second smoothly contoured elongated sidewall passage to further dampen the flow of insufflation gas flowing therethrough to maintain a low fluid resistance stabilized fluid regime upstream of the trocar cannula therein;
   heating and hydrating the insufflation gas on the go in an annular chamber within the trocar by directing the insufflation gas through an inner cylindrical cannula member passing through the conditioning media after flowing the insufflation gas through the fluid stabilizer; and
   delivering a conditioned insufflation gas directly to the body cavity by flowing the conditioned insufflation gas through an annular plenum chamber in the trocar where the annular plenum chamber is located downstream of the annular chamber for heating and hydrating the fluid insufflation gas.

2. The method of claim 1 wherein the method includes the step of attaching a cannula adapter to the cannula and to an insufflation needle to deliver the insufflation gas into the body cavity through the cannula, the adapter and the insufflation needle while the insufflation gas is conditioned on-the-go in the trocar.

3. The method of claim 2 wherein the insufflation is performed in at least two stages, an initial insufflation of a body cavity performed during the medical surgical procedure by directing the insufflation gas through the cannula the cannula adapter and the insufflation needle and a subsequent insufflation of the body cavity performed after removing the insufflation needle and the cannula adapter from the cannula and inserting the cannula directly into the body cavity to thereby direct the insufflation gas directly into the body cavity through the cannula.

4. The method of claim 2 including the step of directing the insufflation gas through at least four inline plenum chambers prior to delivery of the conditioned insufflation gas to the body cavity wherein at least two of the inline plenum chambers are located in the fluid stabilizer and at least two of the inline plenum chambers are annular plenum chambers located in the trocar with at least one of the annular plenum chambers is located upstream of a heating element in a trocar housing and the other located downstream of the heating element in the trocar housing.

5. The method of claim 1 wherein the cannula adapter is coupled to the insufflation needle and to the cannula with a leak proof seal therebetween.

* * * * *